United States Patent [19]

Toth et al.

[11] Patent Number: 4,569,919

[45] Date of Patent: Feb. 11, 1986

[54] IMMUNOLOGIC LATEX AGGLUTINATION PROCESS

[75] Inventors: Tibor Toth; Gerhard Münscher, both of Marburg, Fed. Rep. of Germany

[73] Assignee: Behringwerke Aktiengesellschaft, Fed. Rep. of Germany

[21] Appl. No.: 469,238

[22] Filed: Feb. 24, 1983

[30] Foreign Application Priority Data

Feb. 25, 1982 [DE] Fed. Rep. of Germany ....... 3206729

[51] Int. Cl.[4] ................. G01N 33/544; G01N 33/545; G01N 33/549; G01N 33/546
[52] U.S. Cl. .................................... 436/533; 436/528; 436/531; 436/532; 436/534
[58] Field of Search ............... 436/533, 528, 531, 532, 436/534

[56] References Cited

FOREIGN PATENT DOCUMENTS 2755689  6/1978  Fed. Rep. of Germany ...... 436/528

OTHER PUBLICATIONS

Oreskes, I. et al., Journal of Immunology, vol. 86, pp. 338–343, (1961).

Primary Examiner—Sidney Marantz
Assistant Examiner—Stephen C. Wieder
Attorney, Agent, or Firm—Finnegan, Henderson, Farabow, Garrett & Dunner

[57] ABSTRACT

A latex agglutination process for the detection and determination of a partner of an antigen-antibody reaction is described, wherein an antigen and an antibody are reacted in the presence of a gamma globulin containing no antibodies specific for the antigen.

2 Claims, No Drawings

IMMUNOLOGIC LATEX AGGLUTINATION PROCESS

The present invention relates to a latex agglutination process for the detection or for the determination of a partner of an antigen-antibody reaction in the presence of a gamma globulin containing no antibodies specific for the antigen.

It is known that specific antibodies are bound to the corresponding antigens or haptens. A great number of immunoassays is based on this reaction. Human sera can be tested for the presence of a very defined antigen using the corresponding antibody, for example by means of the competitive binding reaction or of the latex agglutination reaction. These processes and similar processes are well known to those skilled in the art.

These methods may be confronted with the problem consisting in the fact that other constituents present in the serum to be tested may have a troublesome influence. The human serum contains in particular the protein C1q (a complement component) and rheumatiod factors (RF). These substances are both bound to the antibody. The quantities of rheumatiod factors and C1q present in human sera may vary within wide limits. Owing to this fact it is therefore required in general to treat said sera prior to tests of the above type to inactivate C1q or to remove endogenous rheumatiod factors. Otherwise the results and in particular the quantitative determinations may present considerable errors.

The detection of antigens or antibodies with the aid of the latex agglutination reaction has the advantage that it can be done in easy manner and that the test results are obtained within a very short period of time.

It has now been found surprisingly that the aforesaid difficulties caused by a non-specific agglutination of latex particles can be prevented by carrying out the latex agglutination reaction in the presence of a gamma globulin or a gamma globulin fraction which latter does not react with the antigen to be determined.

Subject of the present invention therefore is a latex agglutination process, which comprises contacting latex particles loaded with a partner of an immunologic reaction with a solution of the corresponding partner in the presence of a gamma globulin which contains no antibodies specific for the antigenic partner. Gamma globulins of this type suitable for preventing a non-specific agglutination are gamma globulins of animal origin or human gamma globulins aggregated by heat. Gamma globulin fractions are obtained by known processes, for example, by ammonium sulfate precipitation or by ion exchanger chromatography.

The process according to the invention is applicable to all reactions for the detection of immunologially active substances contained in the blood (serum or plasma) of mammals, in particular of men. Serum proteins are an example of such immunologically active substances.

Suitable latex particles to be loaded (sensibilized) with the immunologically active substances are all latices suitable for use in the latex agglutination test. Examples hereof are homo- and copolymers of styrene. Latices having a particle size of from 0.05 to 0.6 μm are preferred.

The aforesaid latex particles are sensibilized with the antigens or antibodies according to known methods. It is preferred to load the latex with antibodies against serum proteins such as myoglobin, beta 2-microglobulin or immunoglobulin E, human hormones such as human choriogonadotropin, enzymes such as pancreas lipase or animal hormones such as Pregnant mare serum gonadotropin. Sensibilization is done in the following manner: The gamma globulins are precipitated from an antiserum in usual manner, for example using ammonium sulfate, the gamma globulin fraction is dialyzed and concentrated to 30–50 g/l. Alternatively, pure antibody solutions can be obtained by immunoadsorption, which are subsequently concentrated to 2–10 g/l. The antibody solution is added to a suspension of the latex particles having a concentration of about 100 g/l and the batch is incubated for 0.5 to 5 hours at a temperature of from about 20° to 60° C. That portion of the antibodies that is not bound to the latex particles can be removed by centrifugation and resuspension of the solids. Prior to use, the reagent may be resuspended in a buffer solution, preferably glycin-NaCl buffer of pH 7 8.5, to which a protein, for example bovine or human albumin, may be added. The antisera appropriate for use are obtained by immunizing animals in particular rabbits, sheep or goats with a protein of human or animal origin, which protein must be free of the protein to be determined in the test in question.

Examples of such antisera are: anti-human-IgG-serum of rabbits, anti-human-IgM-serum of rabbits, anti-sheep-erthroyte-serum of rabbits, anti-human-IgG-serum of sheep, anti-rabbits-γ-globulin-serum of sheep. The anti-sheep-erythrocyte-serum of rabbits is particularly appropriate. Immunization is done according to known methods. The immunization dose and the immunization time depend on the immunogenity and on the molecular weight of the protein.

The gamma globulin solution is added to the solution, in which an antigen or an antibody is to be detected or determined, preferably in a ratio of from 1:0.1 to 2:0.1 (v:v). The following examples serve to illustrate the invention:

EXAMPLE 1

A latex reagent prepared according to the state of the art containing as specific antibodies antibodies against human myoglobin of rabbits obtained by immunoadsorption and bound to latex particles was used in the following test. The sensitivity of the reagent was adjusted to about 80 ng/ml with the aid of a standard and the test was carried out in the following manner:

1 Drop of diluted human serum (50 μl) to be tested was placed on one field of a test plate. 5 μl of a gamma globulin solution containing no antibodies against human myoglobulin, specifically anti-sheep-erythrocyte-serum of the rabbit, was added and subsequently 1 drop (25 μl) of latex myoglobin reagent was added. After mixing the batch by a stirrer the test plate was moved in rotating manner and examined for agglutination after 3 minutes. In the case of a negative result, the test plate was further moved by rotation and anew tested for agglutination within 2 minutes.

The following table shows the reliability of the process, referred to the determination of myoglobin in the serum:

| Serum Nr. | Presence of rheumatoid factors | Myoglobin RIA (ng/ml) | Latex test state of the art | according to the invention |
| --- | --- | --- | --- | --- |
| 1 | 0 | 110 | + | + |
| 2 | 0 | 320* | + | + |

| Serum Nr. | Presence of rheumatoid factors | Myoglobin RIA (ng/ml) | Latex test state of the art | according to the invention |
|---|---|---|---|---|
| 3 | 0 | 75* | − | − |
| 4 | 0 | 20 | − | − |
| 5 | + | 40 | + | − |
| 6 | + | 20 | + | − |
| 7 | + | 10 | + | − |
| 8 | + | 120 | + | + |

*the limit interesting in clinical practice is to be found at about 80 ng/ml.

As it can be seen from the table, rheumatoid factors in the myoglobin latex test may lead to falsely positive results. When using the sera 5,6 and 7 the latex test according to the state of the art was positive (4th column) although the myglobin RIA (Radio Immuno Assay) as a standard test was negative, since it indicated myoglobin data of 40,20 and 10 ng/ml, these data being inferior to the given clinic data of about 80 ng/ml. The test according to the invention (last column), in contrast thereto, corresponds to the radio immuno test. When using the sera 1 to 4 that contain no disturbing constituents (rheumatoid factors) the results obtained are identical in both latex tests and correspond to those obtained in the RIA.

EXAMPLE 2

A latex reagent prepared according to the state of the art containing as specific antibodies antibodies against PMSG of the rabbit bound to latex particles was used in the following test according to the invention. The sensitivity of the reagent was adjusted to about 2 IU/ml with the aid of a standard and the test was carried out in the following manner:

1 Drop of undiluted mare serum (50 μl) was placed on one field of a test plate, 25 μl of a gamma globulin solution (anti-sheep-erythrocyte-serum of the rabbit) were added and subsequently 1 drop (25 μl) of latex Pregnant mare serum gonadotropin reagent. After thorough mixing by a stirrer the test plate was moved by rotation and tested for agglutination after one minute. In the case of a negative result the test plate was further moved by rotation and tested anew for agglutination within 2 minutes.

The following table shows the comparative results of pregnancy tests on mares:

| Serum of mare | Latex test invention | according to the state of the art | Rectal examination |
|---|---|---|---|
| 1 | − | − | − |
| 2 | − | + | − |
| 3 | − | + | − |
| 4 | + | + | + |
| 5 | + | + | + |
| 6 | + | + | + |

Two of the sera showed a positive result in the latex test according to the state of the art (sera 2 and 3), although the rectal examination did not indicate pregnancy. The results of the test according to the invention, however, corresponded in all cases to the result of the rectal examination.

What is claimed is:

1. A latex agglutination process for the detection or determination of a partner of an immunologic reaction by means of a corresponding partner, which comprises carrying out the detection or determination in the presence of an anti-sheep-erythrocyte-serum of a mammal containing no antibodies specific for the antigenic partner.

2. A latex agglutination process for the detection or determination of a partner of an immunologic reaction by means of a corresponding partner, which comprises carrying out the detection or determination in the presence of an anti-sheep-erythrocyte-serum of a rabbit containing no antibodies specific for the antigenic partner.

* * * * *